United States Patent
Sorenson

(10) Patent No.: US 7,406,385 B2
(45) Date of Patent: Jul. 29, 2008

(54) SYSTEM AND METHOD FOR CONSENSUS-CALLING WITH PER-BASE QUALITY VALUES FOR SAMPLE ASSEMBLIES

(75) Inventor: Jon M. Sorenson, Oakland, CA (US)

(73) Assignee: Applera Corporation, Foster City, CA (US)

( * ) Notice: Subject to any disclaimer, the term of this patent is extended or adjusted under 35 U.S.C. 154(b) by 502 days.

(21) Appl. No.: 10/279,746

(22) Filed: Oct. 23, 2002

(65) Prior Publication Data

US 2004/0053246 A1   Mar. 18, 2004

Related U.S. Application Data

(60) Provisional application No. 60/396,240, filed on Jul. 15, 2002, provisional application No. 60/336,278, filed on Oct. 25, 2001.

(51) Int. Cl.
*G06F 19/00* (2006.01)
*C12Q 1/68* (2006.01)

(52) U.S. Cl. ............................................. 702/20; 435/6

(58) Field of Classification Search ........................ None
See application file for complete search history.

(56) References Cited

U.S. PATENT DOCUMENTS 6,681,186 B1 * 1/2004 Denisov et al. ............... 702/20

OTHER PUBLICATIONS

Huang, X. and Mada A. "CAP3: A DNA Sequence Assembly Program," *Genome Research*, vol. 9, 1999, pp. 868-877.

Nickerson, Deborah A. et al. "PolyPhred: automating the detection and genotyping of single nucleotide substitutions using fluorescence-based resequencing," *Nucleic Acids Research*, Oxford University Press, Surrey, GB, vol. 25, No. 14, 1997, pp. 2745-2751.

Staden, R. "Automation of the computer handling of gel reading data produced by the shotgun method of DNA sequencing", *Nucleic Acids Research*, Oxford University Press, Surrey, GB, vol. 10, No. 15; Aug. 11, 1982, pp. 4731-4751.

Bonfield, J.K. et al. "The application of numerical estimates of base calling accuracy to DNA sequencing projects", *Nucleic Acids Research*, Oxford University Press, Surrey, GB, vol. 23, No. 8, 1995, pp. 1406-1410.

Ewing, B. et al. "Base-Calling of Automated Sequencer Traces Using Phred. I. Accuracy Assessment," *Genome Research*, Cold Spring Harbor Laboratory Press, US, vol. 8, 1998, pp. 175-185.

Ewing, B. et al. "Base-Calling of Automated Sequencer Traces Using Phred. II. Error Probabilities," *Genome Research*, Cold Spring Harbor Laboratory Press, U.S., vol. 8, 1998, pp. 186-194.

Allex, C.F. et al. "Neural network input representations that produce accurate consensus sequences from DNA fragment assemblies," *Bioinformatics*, Oxford, vol. 15, No. 9, Sep. 1999, pp. 723-728.

Gordon, David et al. "Consed: A Graphical Tool for Sequence Finishing," *Genome Research*, vol. 8, No. 3, Mar. 1998, pp. 195-202.

* cited by examiner

*Primary Examiner*—Lori A Clow

(57) ABSTRACT

The present teachings disclose a method for evaluation of a polynucleotide sequence using a consensus-based analysis approach. The sequence analysis method utilizes quality values for a plurality of aligned sequence fragments to identify consensus basecalls and calculate associated consensus quality values. The disclosed method is applicable to resolution of single nucleotide polymorphisms, mixed-based sequences, heterozygous allelic variants, and heterogeneous polynucleotide samples.

18 Claims, 10 Drawing Sheets

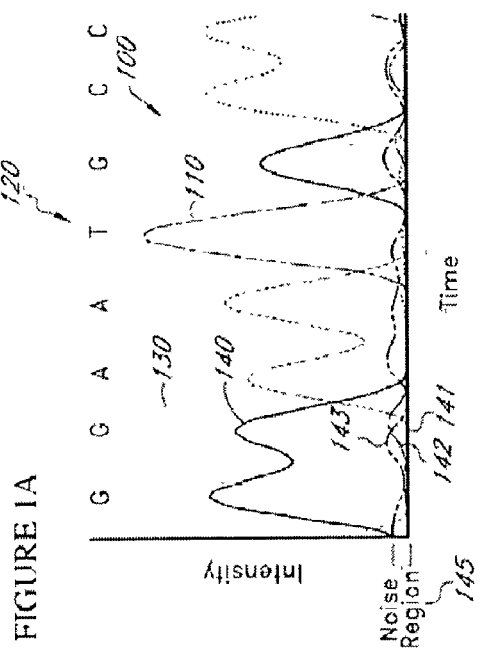

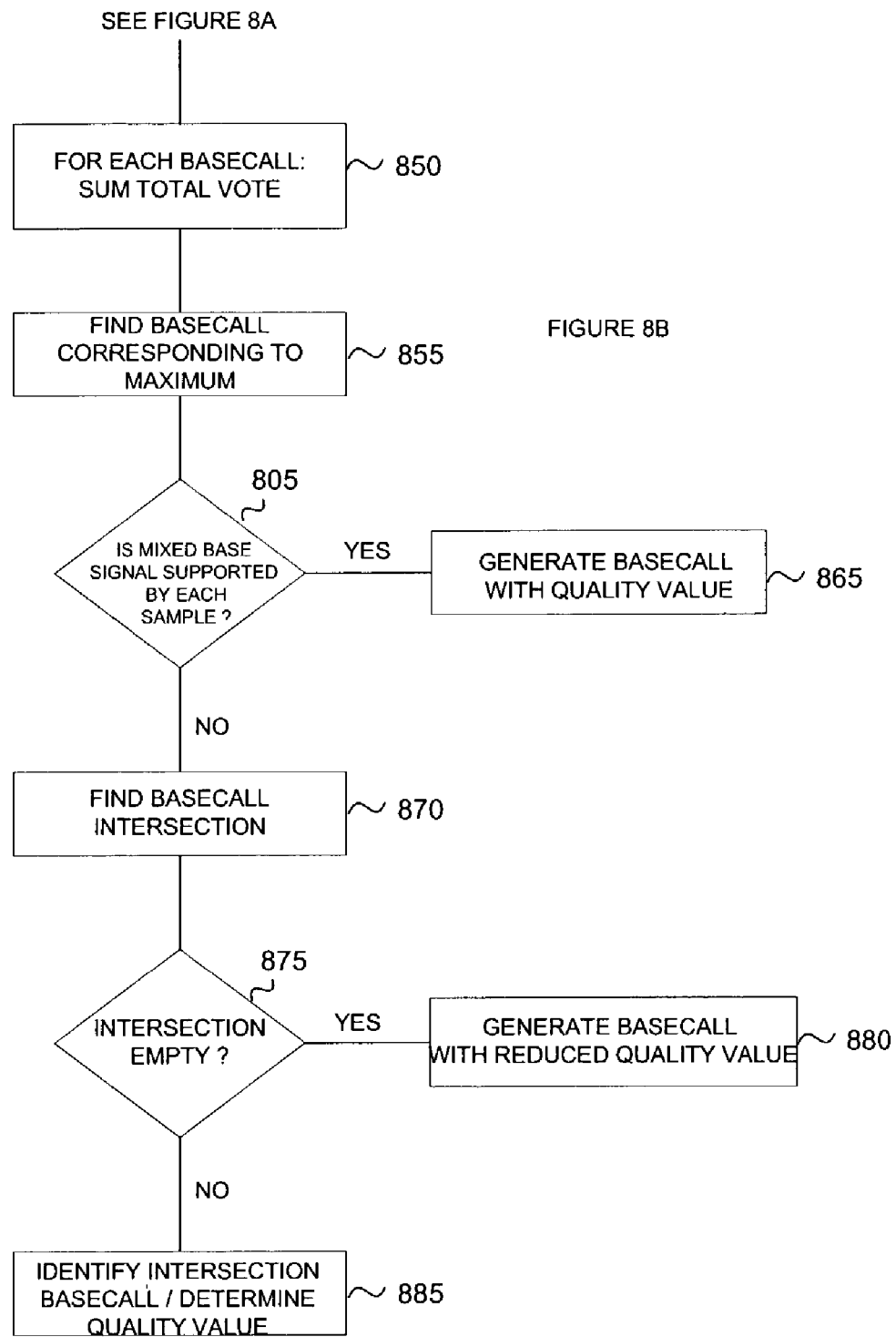

SEQUENCE LISTING

<160> NUMBER OF SEQ ID NOS: 1

<210> SEQ ID NO 1
<211> LENGTH: 38
<212> TYPE: DNA
<213> ORGANISM: Artificial Sequence
<220> FEATURE:
<223> OTHER INFORMATION: Sample Sequence for Figure 3

<400> SEQUENCE: 1
aaggtcagtc atgayaggtc catggcaaat tgccaaaa                                    38

SYSTEM AND METHOD FOR CONSENSUS-CALLING WITH PER-BASE QUALITY VALUES FOR SAMPLE ASSEMBLIES

CLAIM OF PRIORITY

This U.S. patent application claims priority to U.S. Provisional Patent Application No. 60/336,278 entitled "A Consensus-Calling Algorithm With Per-Base Quality Values for Sample Assemblies" filed Oct. 25, 2001 and U.S. Provisional Patent Application No. 60/396,240 entitled "Consensus-Calling Algorithm for Mixed Base Analysis" filed Jul. 15, 2002 which are hereby incorporated by reference.

BACKGROUND

1. Field

The present teachings generally relate to nucleic acid analysis, and in various embodiments, to a system and methods for sequence data processing and consensus sequence analysis.

2. Description of the Related Art

Advances in automated nucleic acid sequence analysis have revolutionized the fields of cellular and molecular biology. As a result, it is now feasible to sequence whole genomes as is evidenced by the completion of sequencing the 3-billion-base human genome. When using automated systems, it is important to maintain a high degree of accuracy with respect to the identification of individual nucleotide bases. Oftentimes, base identification is predicated upon raw data obtained from electrophoretic and/or chromatographic information which is resolved to identify each base within a sequence undergoing analysis. Numerous factors may affect this analysis including, for example, the base composition of the sequence, experimental and systematic noise, migration anomalies (compressions and stretches), variations in observed signal strength for the detected bases, and variations in reaction efficiencies. The presence of mixed-bases in a sample may present further difficulties for conventional systems to properly resolve and identify. Mixed-bases may be representative of sequence variants contained within a sample and may arise from allelic variation or genetic heterozygosity. Mixed-bases may also represent regions within a sample sequence where more than one putative base can be identified. Conventional systems may overlook or erroneously identify these regions thereby degrading the accuracy of the sequence analysis. As a result, there is a need for an improved methodology by which mixed-bases can be identified and evaluated.

SUMMARY

In various embodiments, the methods described herein desirably make use of per-base quality values for input sequence fragments and generate a single output quality value for each consensus basecall. In generating this basecall, the methods take into account factors which may undesirably skew many conventional quality value assessment routine. As will be described in greater detail hereinbelow, one method by which such problems are addressed by the present teachings incorporates the use of differential quality value assessment and weighted basecall voting.

An additional feature of the present teachings involves the ability to resolve mixed-basecalls using information from the aligned sequence fragments. Rigorous mixed-basecall resolution may be desirable as it may improve the quality of the output consensus sequence and remove uncertainty related to the presence of mixed-basecalls in the consensus sequence. Furthermore, unlike many conventional methods which may lack the ability to perform detailed analysis on mixed-basecalls, the present teachings may be used to improve mixed-basecall analysis and identify features such sequence heterozygotes, single nucleotide polymorphisms, and heterogeneous sequence mixtures.

In one aspect, the invention comprises an analysis method for evaluating the composition of a sample sequence comprising a plurality of nucleotide bases, the method further comprising: Receiving assembly information for at least one sequence fragment wherein the assembly information comprises a plurality of putative basecalls spanning at least a portion of the sample sequence; Resolving the assembly information to thereby align the putative basecalls; Identifying quality values associated with at least one of the putative basecalls; and Generating a consensus basecall and a consensus quality value for each of the aligned putative basecalls wherein the consensus basecall corresponds to a predicted base within the sample sequence and the consensus quality value corresponds to a calculated degree of confidence in the consensus basecall obtained, in part, from the quality values for the at least one putative basecalls.

In another aspect, the invention comprises a basecalling method for predicting the composition of a polynucleotide sequence, the method further comprising: Receiving information for a plurality of sequence fragments comprising basecalls spanning at least a portion of the sample sequence and corresponding quality values indicative of a calculated degree of confidence in the basecalls; Aligning the plurality of sequence fragments to identify regions of basecall overlap between the sequence fragments; and Calculating a consensus basecall and a consensus quality value for the regions of basecalling overlap in the aligned sequence fragments wherein the consensus quality values are determined using the quality values for the basecalls of the sequence fragments.

In still another aspect, the invention comprises a method for basecall resolution during sequence analysis, the method further comprising: Comparing a plurality of initial basecalls corresponding to one or more overlapping sequence fragments; Identifying agreement between the initial basecalls as a consensus basecall; Performing a re-calling operation when there is a lack of agreement between the initial basecalls using a more rigorous basecalling routine to generate one or more stringent basecalls and thereafter identifying agreement between the initial basecalls and stringent basecalls as the consensus basecall; Performing a weighted vote for those basecalls that lack of agreement between the initial basecall and the stringent basecall to identify the consensus basecall as the basecall with the greatest weighted vote; and Determining a quality value for the consensus basecall.

In a still further aspect, the invention comprises a system for predicting the composition of a polynucleotide sequence, the system further comprising: A sample processing module that receives information for a plurality of sequence fragments, the sample processing module providing functionality for identifying basecalls spanning at least a portion of the sample sequence and corresponding quality values indicative of a calculated degree of confidence in the basecalls; A specimen processing module that assembles the plurality of sequence fragments to identify regions of basecall overlap between the sequence fragments; and A project processing module that calculates a consensus basecall and a consensus quality value for the regions of basecalling overlap in the assembled sequence fragments wherein the consensus quality values are determined using the quality values for the basecalls of the sequence fragments.

In yet another aspect, the invention comprises a system for basecall resolution comprising: At least one module which provides functionality for comparing a plurality of initial basecalls corresponding to one or more overlapping sequence fragments so as to identify agreement between the initial basecalls to generate a consensus basecall; the at least one module further used to perform a re-calling operation when there is a lack of agreement between the initial basecalls using a more rigorous basecalling routine to generate one or more stringent basecalls and thereafter identifying agreement between the initial basecalls and stringent basecalls as the consensus basecall; the at least one module further performing a weighted vote for those basecalls that lack of agreement between the initial basecall and the stringent basecall to identify the consensus basecall as the basecall with the greatest weighted vote and thereafter determining a quality value for the consensus basecall.

BRIEF DESCRIPTION OF THE DRAWINGS

These and other aspects, advantages, and novel features of the present teachings will become apparent upon reading the following detailed description and upon reference to the accompanying drawings. In the drawings, similar elements have similar reference numerals.

FIGS. 1A,B illustrate exemplary chromatograms for sample polynucleotides with exemplary sequences (SEQ ID NO: 1 & SEQ ID NO: 2).

FIGS. 2A,B illustrate exemplary chromatograms having mixed-base features with exemplary sequences (SEQ ID NO: 3 & SEQ ID NO: 4).

FIG. 8B is a flowchart illustrating one embodiment of a consensus-basecalling method for mixed-base analysis.

DESCRIPTION OF THE CERTAIN EMBODIMENTS

Figure 3:
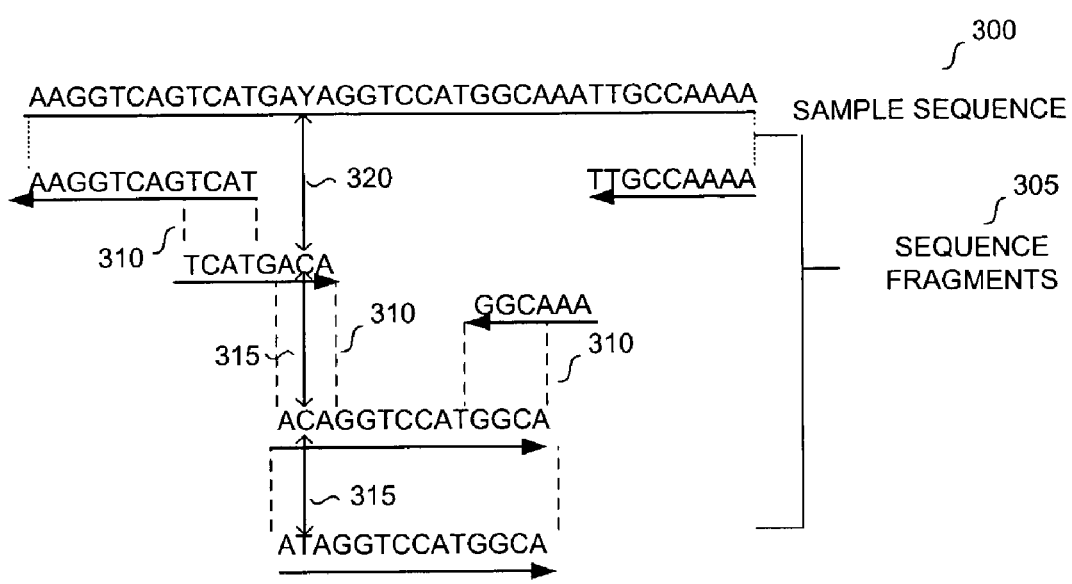
FIG. 3 illustrates an exemplary consensus sequence assembly with exemplary sequences (SEQ ID NO: 5, SEQ ID NO: 6, SEQ ID NO: 7, SEQ ID NO: 8, SEQ ID NO: 9, SEQ ID NO: 10, SEQ ID NO: 11).

Reference will now be made to the drawings wherein like numerals refer to like elements throughout. As used herein, "target", "target polynucleotide", "target sequence" and "target base sequence" and the like refer to a specific polynucleotide sequence that is subjected to any of a number of sequencing methods used to determine its base composition (e.g. base sequence). The target sequence may be composed of DNA, RNA, analogs thereof, or combinations thereof. The target may further be single-stranded or double-stranded. In sequencing processes, the target polynucleotide that forms a hybridization duplex with a sequencing primer may also be referred to as a "template". A template serves as a pattern for the synthesis of a complementary polynucleotide (Concise Dictionary of Biomedicine and Molecular Biology, (1996) CPL Scientific Publishing Services, CRC Press, Newbury, UK). The target sequence may be derived from any living or once living organism, including but not limited to prokaryote, eukaryote, plant, animal, and virus, as well as synthetic and/ or recombinant target sequences.

Furthermore, as used herein, "sample assembly" and "assembly" refer to the reassembly or consensus analysis of smaller nucleotide sequences or fragments, arising from individually sequenced samples that may comprise at least a portion of a target sequence. By combining the information obtained from these fragments a "consensus sequence" may be identified that reflects the experimentally determined base composition for the target sequence.

Nucleic acid sequencing, according to the present teachings, may be performed using enzymatic dideoxy chain-termination methods. Briefly described, these methods utilize oligonucleotide primers complementary to sites on a target sequence of interest. For each of the four possible bases (adenine, guanine, cytosine, thymine), a mixed population of labeled fragments complementary to a least a portion of the target sequence may be generated by enzymatic extension of the primer. The fragments contained in each population may then be separated by relative size using electrophoretic methods, such as gel or capillary electrophoresis, to generate a characteristic pattern or trace. Using knowledge of the terminal base composition of the oligonucleotide primers along with the trace information generated for each reaction allows for the base sequence of the target to be deduced. For a more detailed description of sequencing methodologies the reader is referred to *DNA sequencing with chain-terminating inhibitors,* Sanger et. al., (1977) and *A system for rapid DNA sequencing with fluorescent chain-terminating dideoxynucleotides,* Prober et al. (1987).

The aforementioned sequencing methodology may be adapted to automated routines so as to permit rapid identification of sample sequence compositions. In one exemplary automated application, polynucleotide fragments corresponding to the sample sequence are labeled with fluorescent dyes to distinguish and independently resolve each of the four bases in a combined reaction. In one aspect, a laser tuned to the excitation wavelength of each dye may be used in combination with a selected electrophoretic resolving/separation method to generate a distinguishable signal for each base. A detector may then transform the emission or intensity signal information into a chromatographic trace representative of the composition of the sample sequence. The resulting data may then be subsequently processed by computerized methods to determine the base sequence for the sample. For a more detailed description of a conventional automated sequencing system the reader is referred to *DNA Sequencing Analysis: Chemistry and Safety Guide* ABI PRISM 377 (Applied Biosystems, CA), and *ABI PRISM SeqScape™ Software Version 1.1 User Guide* (Applied Biosystems, CA).

FIG. 1A illustrates a portion of an exemplary chromatographic trace or chromatogram 100 for a sample polynucleotide that may be subjected to automated analysis in the aforementioned manner. The trace comprises fluorescence information translated into a series of peaks 110 for each of the bases, with each peak 110 representative of the detected signal or intensity for one of the four bases (G, A, T, C). This information may be plotted as a function of time and the composition of the sample sequence may be identified by determining the order of appearance of peaks 110 in the chromatogram. When evaluating each peak's intensity relative to other peaks in the same localized region, a basecall may be made which identifies the base that is likely to be present at the selected position. Generally, each base position in the chromatograph corresponds to a single predominate peak that may be related to the base at that position within the sample sequence. For example, a base sequence 120 corresponding to 'GGAATGCC' (SEQ ID NO.1) is identified by the trace 100.

One confounding characteristic of many sequencing traces that may affect the basecalling accuracy of conventional systems is that for any given peak position, signals may be present which correspond to one or more of the bases. Thus, for a selected peak position 130, a plurality of signal components 140-143 may be observed, which may correspond to a G-signal component 140, an A-signal component 141, a T-signal component 142, and/or a C-signal component 143. The intensity of each detected base component is related to many factors and may include noise and reaction efficiency variations.

In one aspect, when performing base identification or "basecalling" it is necessary to distinguish spurious or noise-related signals 145 from the base peaks 140 corresponding to the actual base present within the selected peak position 130. To this end, basecalling operations may incorporate functions that manipulate and/or normalize the chromatographic data to account for systematic and experimental variations to thereby aid in the resolution and identification of bases corresponding to each of the peaks at the selected peak positions.

When analyzing chromatographic traces, for each selected peak position 130 there may be two or more identifiable peaks indicating a single basecall may not be the appropriate basecall. FIG. 1B illustrates an exemplary chromatographic trace 150 having two or more identifiable peaks for a selected peak position 130 wherein a G-signal component 160 and an A-signal component 161 are present. The intensity of each signal component 160-161 may be such that the "true" basecall for this position within the sample sequence is not immediately obvious. In the illustrated embodiment, the basecall for the selected peak position 130 might be interpreted as either 'G' and/or 'A'. In the absence of additional data a value of 'R' might therefore be assigned to the selected peak position 130. According to the example described above, in instances where the base identity for a selected peak position 130 remains uncertain, the constituent bases may be identified to generate a compound or mixed-basecall. Many conventional sequence analysis methodologies are limited with respect to their ability to resolve mixed-basecalls and as a result the identified sequence may contain undesirable regions of uncertainty wherein the identity of the base cannot be reported with substantial certainty.

An important consideration when identifying mixed-bases within a sample sequence is that the actual base composition at the region of where the mixed-base is observed may reflect a single base or more than one base. As shown in FIG. 2A an exemplary chromatogram 200 having a candidate mixed-base 'Y' at the selected peak position 130 arises from a single sample sequence 'GGAATGCC'. In this instance, one of the two identified signal components 205, 210 may arise from an actual sample sequence base with the second signal component representative of nonspecific or fluorescence unrelated to the base composition of the target. The nonspecific fluorescence may further result, for example, from anomalous instrumental/reaction variations and/or noise that may appear within the chromatographic trace as a putative base signal.

In FIG. 2B an exemplary chromatogram 250 having a candidate mixed-base 'S' at the selected peak position 130 may arise from two sample sequences 'GGAATGCC' (SEQ ID NO. 1) and 'GGAATCCC' (SEQ ID NO. 3). In this instance, both identified peak components 255, 260 may be representative of discrete bases both of which may be present in the sample. It will be appreciated that mixed-base presence as described above may result from allelic variations and/or genetic heterozygosity in the sample giving rises to two or more discrete sequences. In various embodiments, the present teachings desirably improve the ability to distinguish mixed-base chromatogram characteristics and may improve recognition and identification of sample sequences containing more than one sequence variant. Unlike conventional systems which may overlook or misidentify sequence related information in the region of mixed-bases, various embodiments of the present teachings describe specialized routines that may aid in the identification of mixed-base regions. Additionally, as will be described in greater detail hereinbelow, these methods may desirably improve the accuracy of discriminating between sequence variations and mixed-bases whose composition resolves to a single base. Furthermore, various embodiments of the present teachings desirably evaluate quality values assigned to sequence fragments and produce a single consensus quality value. The consensus quality value may be useful in better understanding the estimated accuracy of each basecall including pure-bases, mixed-bases, and gaps identified by the automated sequencing routines.

Consensus sequence analysis is one method for improving the accuracy of basecalling, including discrimination in mixed-base regions, and may be used to assess multiple sample sequence fragments. In one aspect, consensus sequencing comprises an evaluation of redundant or overlapping sequence fragments that correspond to at least a portion of the sample sequence of interest. During this analysis, the results from the sequence fragments are included in a combined analysis wherein some overlapping or redundant sequence information may be obtained for the sample sequence. Using redundant sequence information in this manner provides a means to improve the validation of basecalls as compared to single sequence fragment analysis alone.

FIG. 3 illustrates an exemplary consensus sequence based approach that may be used in conjunction with the present teachings wherein the base sequence 300 for a sample is determined by assembling the results from a plurality of sample sequence fragments 305. When performing sequencing in this manner, sequence fragments 305, typically of various sizes and orientations, may be independently sequenced. Using sequence comparison routines, regions of homology 310 between sequence fragments 305 may be observed. These regions 310 may further be used to position and orient the sequence fragments 305 with respect to one another to obtain the assembled consensus sequence which in one aspect is reflective of the experimentally determined sample sequence. Using overlapping or redundant regions of sequence homology 310 between sequence fragments 305 additionally provides a means for validating the sequence and may further be used in identification of mixed-bases. As previously indicated, a mixed-base may be called when there are two or more peaks present in the selected peak position of the electropherogram. These peaks may correspond to distinguishable bases 315 in the sequence fragments 305 ('C' and 'T' in the illustrated example) and may generate a mixed-basecall in the sample sequence 320 ('Y' in the illustrated example). In one aspect, the difference between bases for a selected position in a sample sequence may be indicative of heterozygosity for an allele being sequenced and may suggest the presence of a single nucleotide polymorphism (SNP). Additionally, mixed-bases may arise when sequencing various sample sequences including those obtained from viral or microbial populations, pooled samples, or sequencing of PCR fragments obtained from heterogeneous tissue samples.

The various embodiments of the present teachings provide means for identification of the composition of mixed-base regions and may aid in distinguishing mixed-bases called in these regions from noise or other confounding factors. Additionally, the basecalling methods described herein may be used to resolve mixed-base sequences to identify one or more associated pure-bases. One factor which presents a problem for many conventional systems is the presence of sequencing chemistry noise. Noise of this type may appear in the electropherogram and may possess a similar signature to that of a mixed-base. Improper calling of such noise may result in the generation of undesirable false positive basecalls. In one aspect, false positive basecalls may comprise mixed-base-calls that are in actuality pure (single) bases. Various embodiments of the present teachings desirably avoid or reduce the number of false positive basecalls by comparing information from sequence fragments and associated quality values. Another issue that may complicate mixed-base identification is differential incorporation of dideoxy-nucleotides using enzymes such as sequencing polymerases. Differential incorporation may result in peaks which are not of equal height in the electropherogram. This problem may be further compounded by alleles that may be present in a sample in non-equivalent proportions (e.g. Ratios greater than or less than 50:50). For example, two different sequence variants of an allele may be present in a ratio of 10:90. In such instances, the expected peaks for the corresponding base of the sequence variants may not be resolved or identified with a peak ratio of 10:90 as a result of differential incorporation. Using quality value analysis in the manner described herein, the present teachings may desirably improve the ability to distinguish bases and overcome these potential problems which often confound conventional systems resulting in improved basecalling accuracy.

In various embodiments, the system and methods described herein present a novel approach for determining the base sequence for a target polynucleotide based, in part, upon a consensus calling approach that utilizes per-base quality values along with a dedicated base discrimination method. As will be described in greater detail hereinbelow, this approach may improve basecalling accuracy as compared to that of conventional algorithms and may be readily adapted for use with software analysis packages including SeqScape™ sequence analysis software (Applied Biosystems, CA) and hardware sequencing instrumentation including ABI Prism® DNA Analyzers (Applied Biosystems, CA).

One method for analyzing electropherograms identifies bases of the sample fragments and the resultant assembled sample sequence while assigning quality values (QV) to each of the called bases. (See B. Ewing, et al., "Base Calling Of Automated Sequencer Traces Using Phred. I. Accuracy Assessment", Genome Research, vol. 8(3), pp. 175-185 (1998); B. Ewing and P. Green, "Base-Calling of Automated Sequencer Traces Using Phred. II. Error Probabilities", Genome Research, vol. 8(3), pp. 186-194 (1998)). In these basecalling procedures the quality value represents the measure of reliability for a given basecall and estimates the basecalling error. Generally represented, a probability value (P) may be defined as the probability that a particular basecall is incorrect with a quality value (QV) defined by the expression:

Equation 1: $QV = -10 \log_{10} P$

According to this expression, lower quality values generally indicate a higher probability of basecall error and higher quality values indicate a greater degree of certainty for an accurate basecall. In various embodiments, the consensus-calling methods described herein improve quality value assessment by evaluating per-base quality values for one or more sequence fragments with respect to one another and generating a consensus quality value which, in one aspect, may be indicative of an overall or combined approximation of certainty for the basecalls associated with the sample sequence. It will be appreciated that these methods may adapted for use with existing consensus-calling applications as well as raw and processed sequencing information obtained from numerous sources. Additionally, details of these quality value assessment and error probability estimation routines may be found in commonly assigned U.S. patent application Ser. No. 09/658,161 filed Sep. 8, 2000 and entitled: A system and method for improving the accuracy of DNA sequencing and error probability estimation through application of a mathematical model to the analysis of electropherograms, which is hereby incorporated by reference in its entirety.

Figure 4:
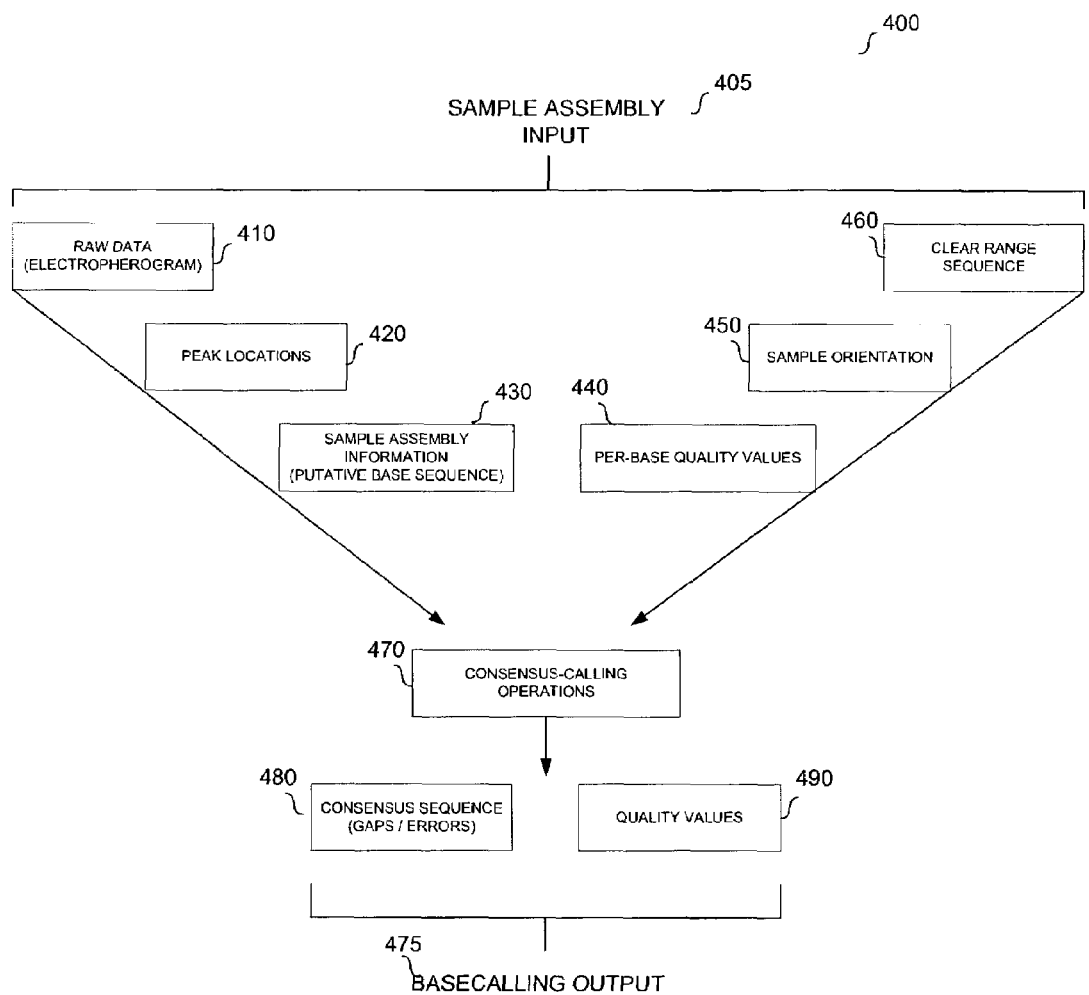
FIG. 4 illustrates an overview of an exemplary analysis schema for consensus sequence analysis.

FIG. 4 illustrates an overview of an exemplary analysis schema 400 in which the consensus-calling methods utilized by various embodiments of the present teachings are used to assemble a sample sequence. The consensus calling methods may operate with numerous forms of sample assembly input 405 including those generated by various types of multiple sequence alignment (MSA) algorithms. For example, the sample assembly input 405 may comprise multiple sequence alignment data obtained from MSA algorithms which align each sample sequence using a reference sequence. Additionally, sample assembly input 405 may comprise information that is generated by MSA algorithms that apply de novo assembly routines including, for example, Phrap, CAP, or other dynamic programming MSAs. The sample assembly input 405 obtained from these algorithms may further include: (a) raw data 410 comprising the electropherogram and/or corresponding intensity values; (b) peak locations 420 indicative of the position of peaks identified within the electropherogram or corresponding data; (c) sample assembly information 430 including putative base sequence data (d) per-base quality values (QV) 440 determined using conventional methodologies including TraceTuner™ and Phred; (e) sample orientations 450 indicative of the relative direction the sequence (e.g. 5'-3' designations); and (f) clear range identifiers 460 indicative of the usable range of basecalls for the sample sequence. As will be described in greater detail hereinbelow, the use of the clear range identifiers 460 aid in the determination of various parameters including γ which may be used to quantify the degree of independence of sequence traces having substantially the same orientation.

It will be appreciated that although the aforementioned exemplary input 405 is illustrated as being received by the consensus-calling methods, at least a portion of this information may be optional or readily calculated by various integrated functions prior to consensus analysis and therefore need not be available prior to consensus analysis. Additionally, various operations may be utilized to convert the input data types and information (such as those produced by Trace-Tuner™ and Phred) into a form compatible with the consensus-calling methods.

As will be described in greater detail hereinbelow, once the desired input data 405 has been acquired and/or calculated, a series of consensus-calling operations 470 may be performed to produce output 475. This output may comprise information such as a consensus sequence 480 and a quality value assessment 490 for each base. In one aspect, the consensus sequence 480 represents the calculated sample sequence assembly which may include a predicted base sequence as well as gap information.

Figure 5A:
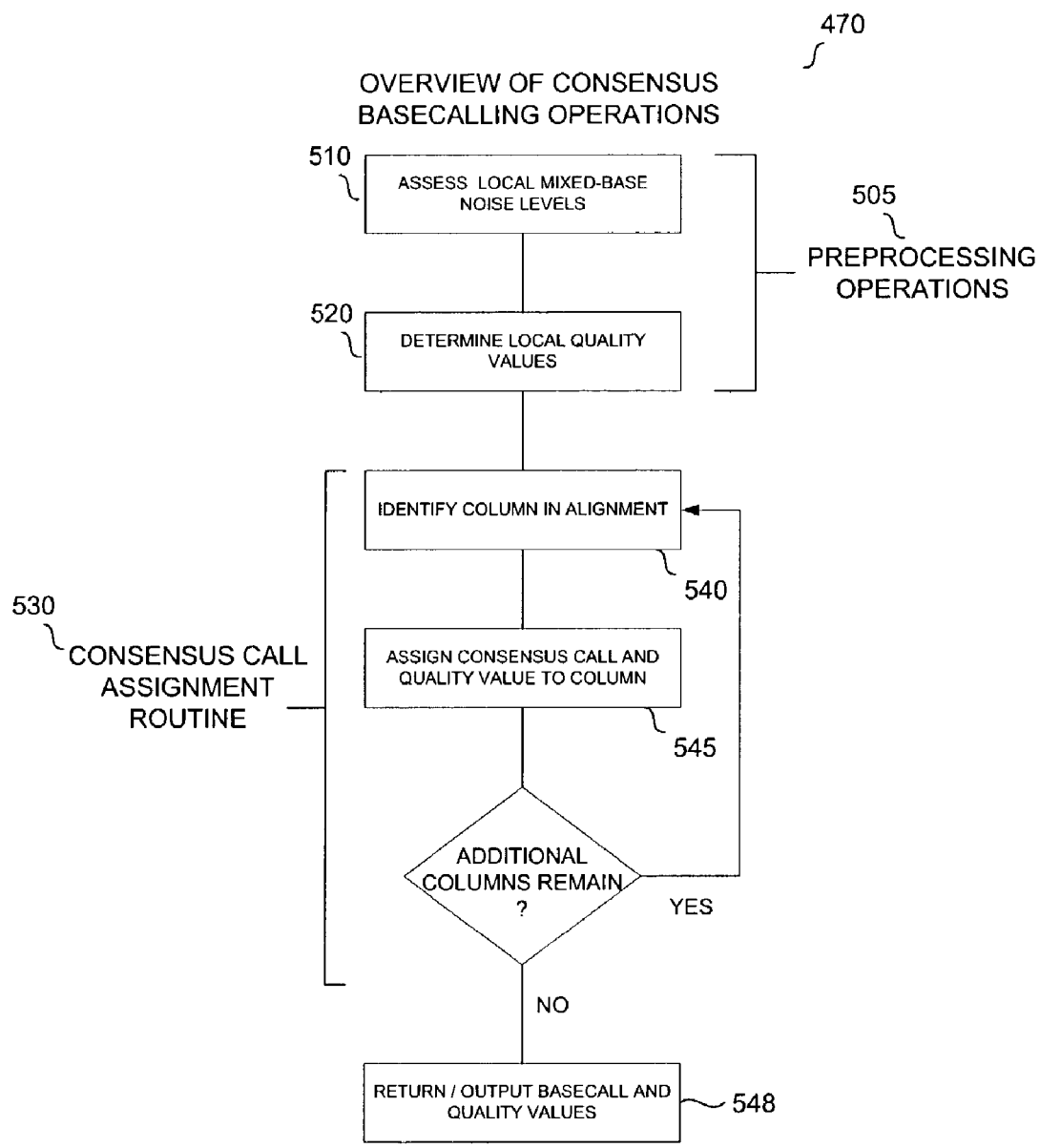
FIG. 5A is a flowchart illustrating one embodiment of a consensus basecalling method.

FIG. 5A illustrates an overview of the consensus-calling operations 470 used to evaluate sample assembly input data 405 and generate output 475 corresponding to the consensus sequence 480 and quality value information 490. In one aspect, the consensus-calling operations 470 may commence with one or more pre-processing operations 505 that may be used to evaluate and calculate information which serves as additional input to the subsequent consensus-calling steps. A first pre-processing operation 505 comprises an assessment of the local mixed-base noise level 510 for each position in the sample sequence. In one aspect, the local mixed-base noise level 510 may be defined as an average of a plurality of nearby mixed-basecalls for each position.

The mixed-base noise level 510 may be obtained using a sliding window averaging approach. In one aspect, the window size may be flexibly defined to accommodate various experimental data types and compositions. In various embodiments the window size ranges between approximately 5-20 base pairs in length. The local mixed-base noise level 510 generally reflects noise that may arise, for example, as a result of chemistry and/or instrumental noise which may be present in the electropherogram at each position. Furthermore, the mixed-base noise level 510 may be used to ascertain the quality of input mixed-basecalls derived from the sample assembly information 430. Additionally, mixed-base noise level determination and may be used to supplement input per-base quality values 440 when evaluating the quality or confidence of the sequence data. An exemplary embodiment of the mixed-base noise assessment operation is provided in FIG. 6A and is described in greater detail hereinbelow. A second preprocessing operation 505 comprises a local quality value assessment 520. In various embodiments, local quality values may be defined as an average over the per-base quality values for each position in the sample sequence. In a manner similar to the assessment of local mixed-base noise levels 510, assessment of local quality values may be performed using a sliding window approach to determine local averages. When determining the local quality values, the average weighting within the window may be differentially adjusted based on user defined preferences. For example, in various embodiments the contribution of the quality values contained in the sliding window may be adjusted towards the center of the window rather than using strictly balanced weighting. Differential weighting in this manner may be desirable and facilitate generation of refined local quality values having a greater degree of basecall confidence. It will be appreciated that the window size used when assessing local quality values 520 need not be of identical size relative to that used in the mixed-base noise level determination 510. For example, in various embodiments the window size used for assessing local quality values may be smaller than the noise level window ranging in size from approximately 5-10 base pairs in length.

One desirable feature of the averaging method for local quality value assessment 520 is that the resultant quality values calculated by this method may provide a smoother estimate of local electropherogram quality for a given position in a sample sequence. Rather than relying solely on quality value information directed towards individual bases, the averaging approach desirably incorporates additional information that helps take into account the local quality of bases in the sequencing trace relative to one another. In one aspect, use of the averaged quality values in the aforementioned manner provides improved input for the consensus calling operations. Furthermore, quality value assessment based on averaged values may provide greater confidence and accuracy when consensus basecalls are subsequently identified. An exemplary embodiment of the local quality value assessment operation is provided in FIG. 7 and is described in greater detail hereinbelow. The use of locally averaged quality values further aids in reducing potential biases introduced into the consensus-calling methods of the present teachings by nuances associated with the underlying basecalling quality-value methods. In various aspects, this feature is desirable as it provides a means to extend the usability of the basecalling approach across many different data types and basecalling methodologies.

In various embodiments following the preprocessing operations 505 (if performed), a consensus call assignment routine 530 is performed. The consensus call assignment routine 530 incorporates a heuristic component which provides a basecalling functionality that simulates an expert approach to assessment and assignment of proper consensus calls and sequence assembly. Unlike other machine learning or classification procedures for consensus calling, the consensus call assignment routine 530 does not necessarily require large annotated data sets for training. Furthermore, while conventional machine learning or classification procedures may not be transparent to the user, resulting in potential complications in data review or program development, the consensus call assignment routine 530 is substantially user-transparent.

A further benefit of the consensus call assignment routine 530 results from the openness of the rule-based approach to consensus calling. As a result the methodology described herein is amenable to selective tuning using particular data sets and applications. Furthermore, development may be facilitated as the assignment routine 530 can be readily modified to accommodate other types of data sets and sample input. For example, it is conceived that the methods described herein may be adapted for use in sequence analysis involving protein or peptide samples in additional to nucleic acid samples.

As will be described in greater detail hereinbelow, the consensus call assignment routine 530 comprises a plurality of steps wherein the input sample assembly information 430 is evaluated to assign a consensus call and quality value for the information. In one aspect, the assignment routine 530 commences with formatting the sample assembly information 430 in a columnar manner 540 wherein sequence fragments that may correspond to overlapping regions of the sample sequence are aligned with respect to one another. Each column of sequence information and corresponding quality values are then evaluated and a consensus basecall and quality value are calculated for each base in the sample sequence in state 545. This procedure may be repeated as necessary for each base in the sample sequence. Thereafter, the results of the consensus-calling assignment routine are returned in state 548 where they may be stored or output to the user. The methods of consensus calling and quality value assignment will be discussed in greater detail hereinbelow with reference to subsequent illustrations and figures.

Figure 5B:
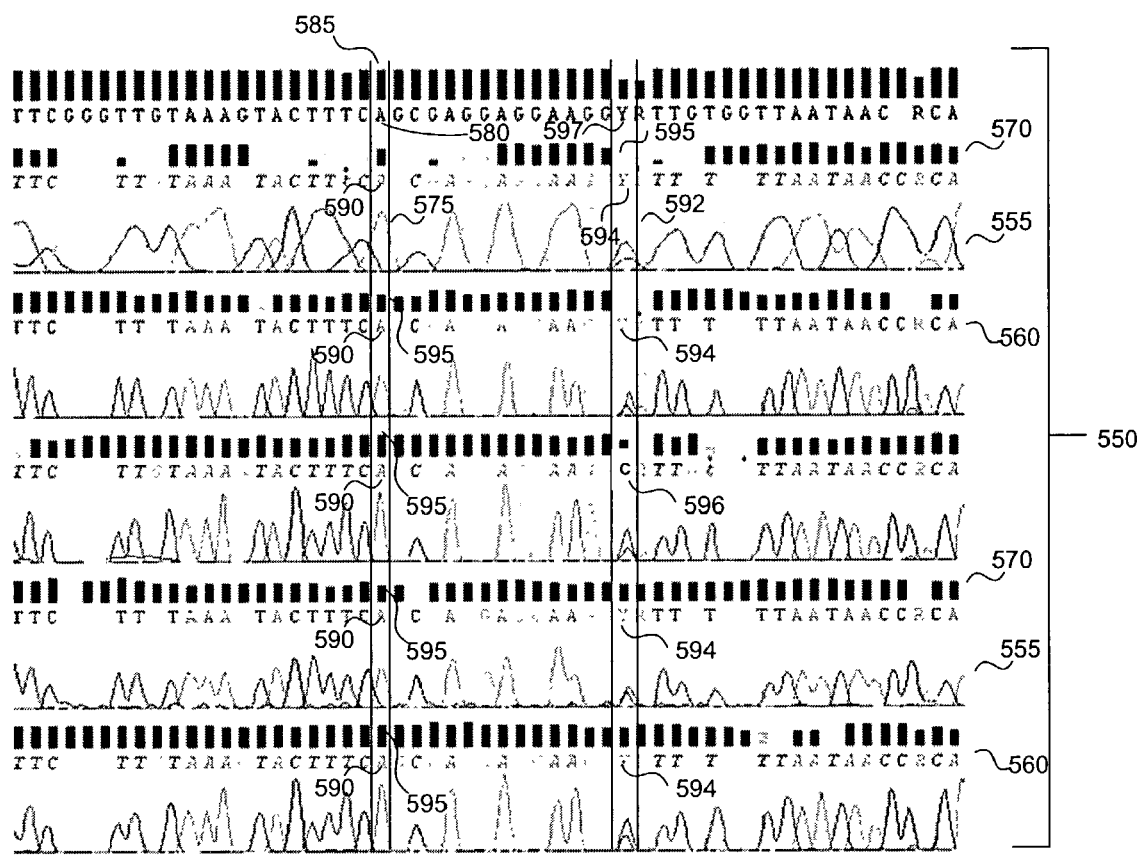
FIG. 5B illustrates an exemplary chromatogram and sample assembly for a plurality of aligned sequence fragments with exemplary sequences (SEQ ID NO: 12 & SEQ ID NO: 13).

FIG. 5B illustrates an exemplary sample assembly for a portion of a sample sequence wherein a plurality of sequence fragments 550 are aligned in a columnar manner with respect to one another. In various embodiments each sequence fragment 550 may be associated with a corresponding electropherogram 555 and a base sequence 560 comprising a plurality of basecalls. Additionally, a quality value 570 may be associated with each base in the basecall sequence 560. For ease of visualization, the quality value 570 may be represented in various ways in addition to a strict numerical value. For example, as shown in the illustrated embodiment the numerical value associated with the quality value 570 may be translated into a bar graph indicative of the calculated result for each quality value 570.

Taken together, the information obtained from the sequence fragments 550 may be used in generating the sample assembly for which consensus basecalls may be made using the aligned data. In one aspect, the information corresponding to a selected base of the sample sequence is processed by identifying a column 575 of sequence fragment information. The information contained in each column is then evaluated using the consensus call assignment routine 530 and a consensus basecall 580 is made. In addition to the consensus basecall 580, a consensus quality value 585 may be calculated and associated with the consensus basecall 580 (shown as a bar in the illustration).

The consensus based approach described above is further illustrated for the columnar sequence 575 where the basecalls 590 for each aligned sequence fragment 550 correspond to 'A' with varying degrees of certainty or confidence represented by the associated quality value 595. Taken together these quality values 595 may be used to generate the consensus quality value 585 which in some instances may be greater than the individual quality values 595 due to the increased number of comparisons being made. It will be appreciated by one of skill in the art that using information including quality values from more than one sequence fragment 550 may aid in increasing the overall confidence in the resulting consensus.

FIG. 5B further illustrates the presence of a mixed-basecall in at least one sample fragment 550 in a second columnar sequence 592. During assembly of the one or more sequence fragments 550, mixed-basecalls 594, representing regions where single bases are not identified, in addition to pure-basecalls 596, represented by single identifiable bases, may be present. As will be described in greater detail hereinbelow, and in various embodiments, mixed-basecalls 594 may be resolved along with their associated quality values 595 using the information from one or more sequence fragments 550 to generate a consensus basecall 597 with improved accuracy and/or confidence. In one aspect, when a mixed-basecall is present in the corresponding aligned sequence fragments, consensus evaluation may be used to aid in the identification of the composition of the mixed-base and distinguish pure-bases from noise. It will be appreciated that the illustrated sequence assembly is but one of many possible permutations of assembly analysis. Additionally the number of sequence fragments used in the comparison is not necessarily limited to the quantity illustrated and may include more or less than the quantity shown while achieving similar results in terms of resolving the composition of the sequence fragments and generating the consensus sequence assembly.

Figure 6A:
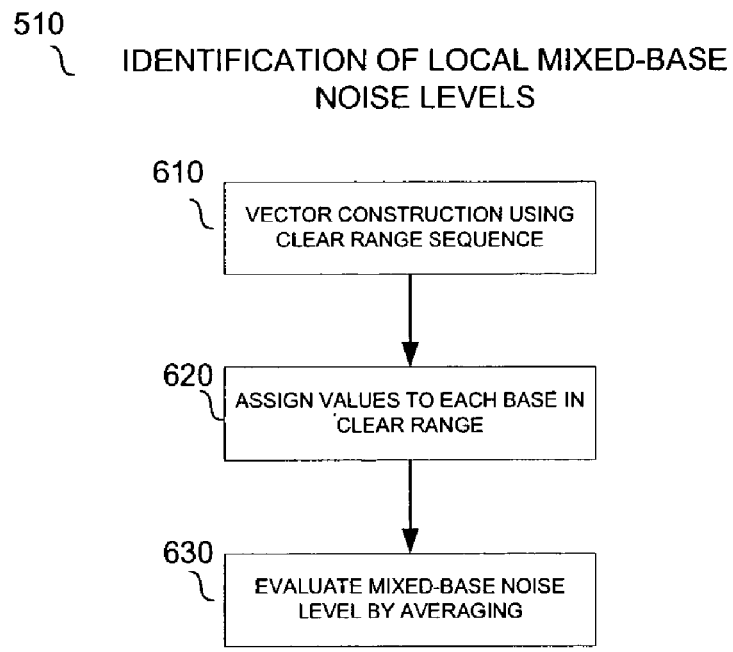
FIG. 6A is a flowchart illustrating one embodiment of a method for identifying local mixed-base noise levels.

FIG. 6A illustrates one embodiment of a method 510 for assessing local mixed-base noise levels according to the pre-processing operation 505 described above. This methodology may be implemented using the previously described sliding window averaging method and may be readily adapted to operate with automated sequence evaluation methods. In one aspect, the method 510 commences in state 610 where a data string or vector is constructed whose length is set according to the length of a clear range sequence that is determined based on the sequence information to be analyzed. In one aspect the clear range sequence may be represented by at least a portion of the sequence information corresponding to the desired region where base assembly will take place. The length of the clear range sequence therefore may be assigned as an integer value which corresponds approximately to the number of basecalls contained in the clear range sequence.

Following vector construction in state 610, the method 600 proceeds to assign a base weighting value to each basecall in state 620 which may be based upon the putative base composition. In one aspect, the weighting value is used to transform each basecall in the clear range into a quantifiable value that may be averaged with other basecalls. Averaging in this manner permits identified basecalls to be differentially weighted according to their composition. For example, it may be desirable to differentially weight pure-bases as compared to mixed-bases and gaps so as to influence the calculated quality value determined during sequence assembly. In various embodiments, the base weighting value may be assigned according to a user-defined rule set where identified mixed-bases (including, for example, R, Y, K, M, S, W) may be assigned a value of '1'. In a similar manner other mixed-bases (including, for example, H, B, V, D, and N) may be assigned a value of '2'. The remaining bases G, A, T, C may be assigned a value of '0'.

Following base value assignment in state 620 the method 510 proceeds to state 630 where an averaging of the basecall values in the clear range may be performed. In one aspect, a sliding window averaging approach is utilized to determine the mixed-base noise level 510 comprising an average of the weighted values for basecalls within the sliding window. This averaging operation may be performed for each basecall within the clear range to generate per-base noise values that may be used in later consensus call assignment routines. Application of mixed-base noise levels in consensus call assignment will subsequently be described in greater detail.

Figure 6B:
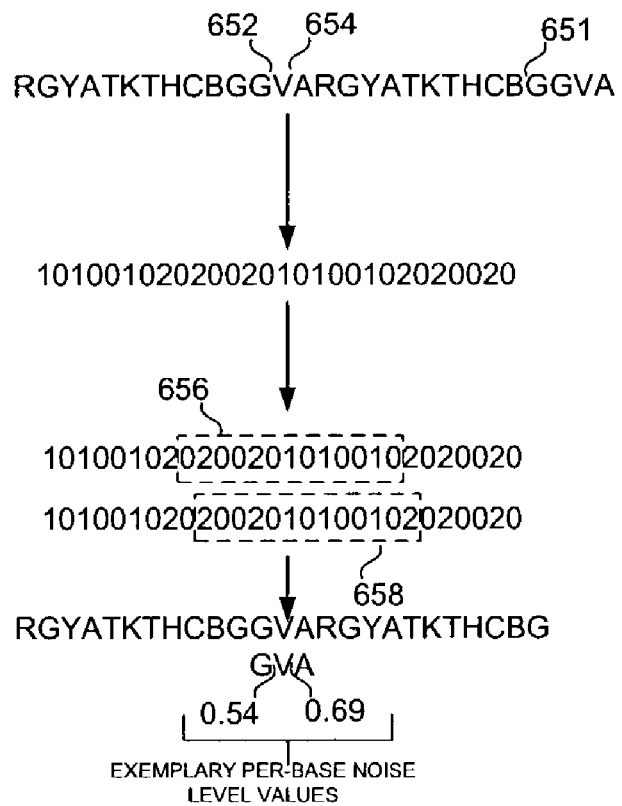
FIG. 6B illustrates an exemplary mixed-base noise level assessment for a sample sequence with exemplary sequences (SEQ ID NO: 14 & SEQ ID NO: 15).

FIG. 6B further illustrates the mixed-base noise level assessment for two exemplary bases 652, 654 in a sample base sequence 651. In one aspect, the base sequence may be represented by a vector construction having the exemplary basecall sequence RGYATTHCBGGVARGYATKTHCBG-GVA (SEQ ID NO. 14). Following the rules for basecall weighting value assignment a new vector may be generated which comprises the numeric sequence '1010010202002010100102020020' wherein each value is associated with a base in the vector construction. As illustrated for the first base 652, the sliding window averaging operation generates a weighted average from the basecall weighting values of approximately '0.54'. Similarly, the second base 654 is associated with a weighted average of approximately '0.69'. Mixed-base noise levels are determined for other basecalls in the clear range region in a substantially similar manner to thereby generate a plurality of individual weighted averages. In one aspect, the size of the sliding window is between approximately 4-20 bases although other sliding window sizes may readily be used to assess the mixed-base noise level.

Figure 7:
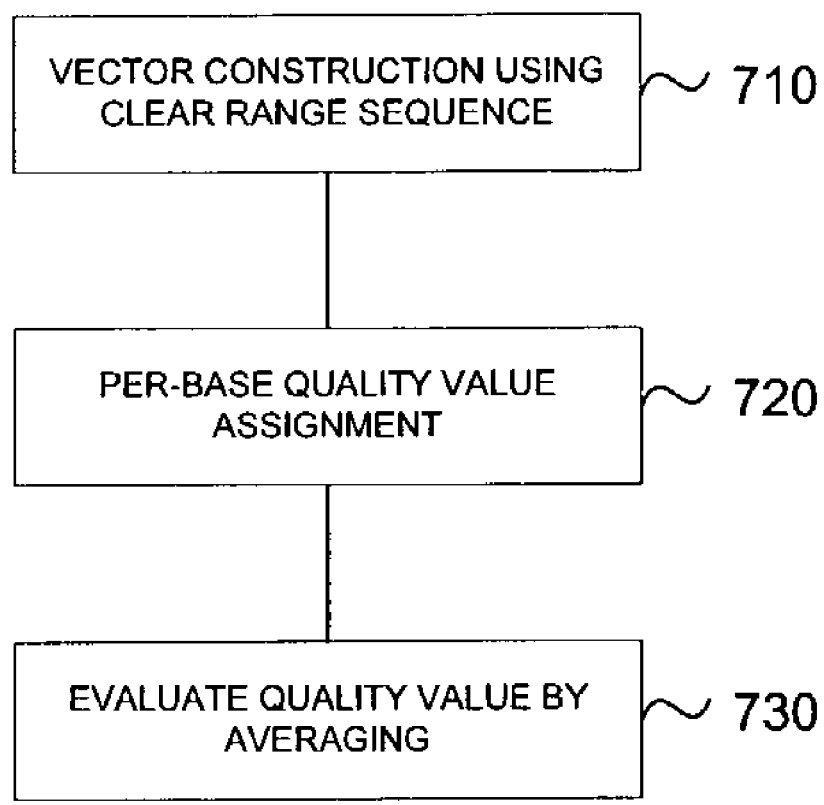
FIG. 7 is a flowchart illustrating one embodiment of a method for local quality values assessment.

FIG. 7 illustrates further details of the local quality value determination methodology 520. In various embodiments, local quality values are calculated in a manner similar to that used in the mixed-base noise level identification routine 510 wherein a sliding window average is obtained for a selected data set. In one aspect, the method 520 commences in a state 710 with the construction of a data string or vector having a length approximately equivalent to the identified clear range sequence. In state 720, quality values are associated with each of the basecalls in the clear range sequence. These quality values may be calculated using the sample assembly input 405 or previously calculated input per-base quality values 440 may be utilized. In state 730, a sliding window local average of the per-base quality values is obtained for each basecall in the clear range sequence. As previously described, it may be desirable to apply a differential weighted average when determining the local quality value for each basecall by weighting the quality values of those bases closer to the center of the sliding window more heavily. As with the window used in the local mixed-base noise level determination 510, the window used in the local quality value determination methodology 520 may be varied in size and need not be identical to that used in the noise level determination 510. In one aspect, determination of local quality values 520 in the aforementioned manner desirably smoothens the electropherogram data for a given position in a sample sequence. Such smoothening of the data may contribute to improved basecalling accuracy when using the system and methods described herein.

Figure 8A:
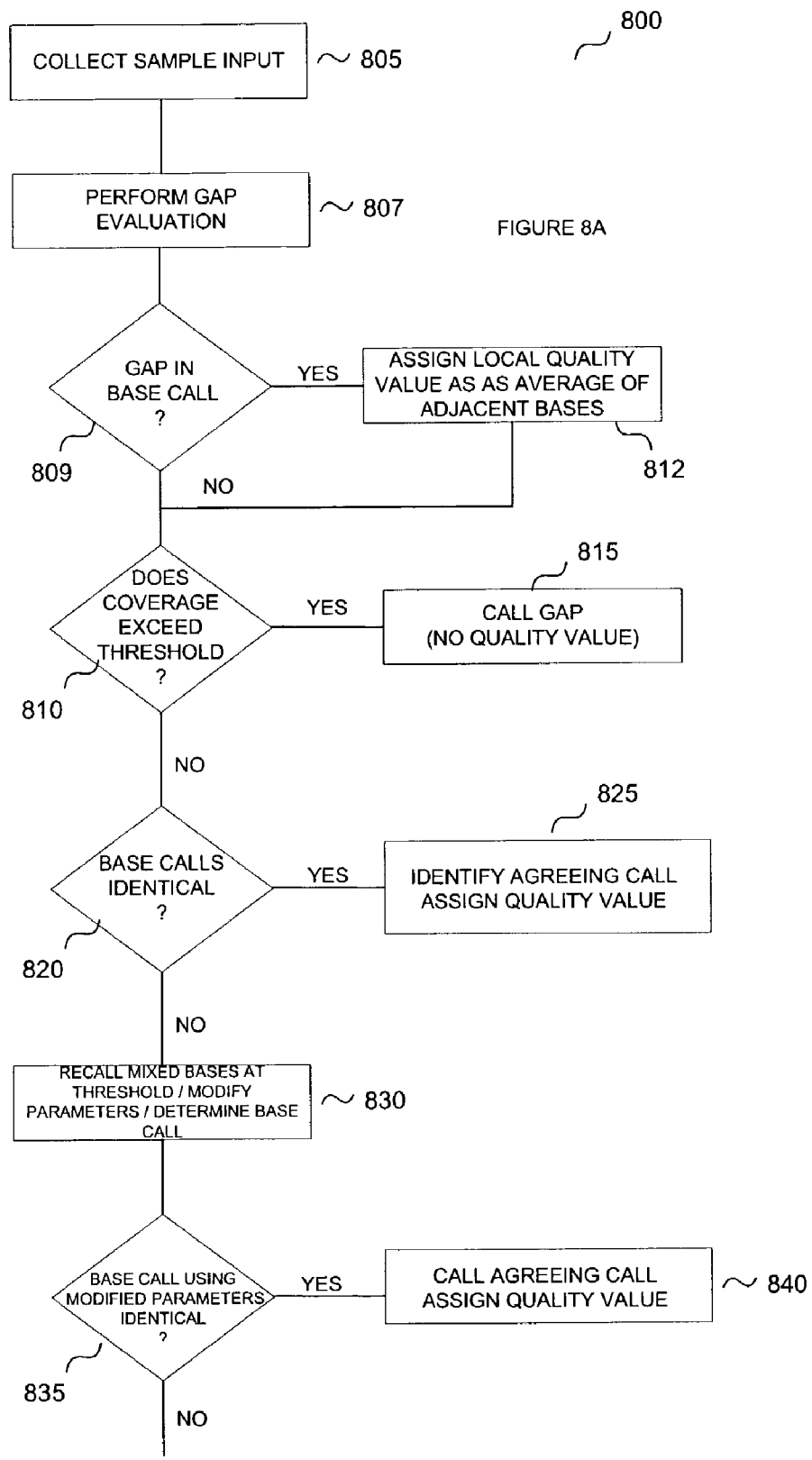
FIG. 8A is a flowchart illustrating one embodiment of a consensus-basecalling method.

FIG. 8A illustrates one embodiment of a consensus-calling method 800 that may be used for assembly of the consensus sequence. As previously described, the method 800 may utilize sample assembly input 405 and/or information produced in the preprocessing operations 505 to generate basecalls that identify the sequence composition using sequence and quality value information obtained for one or more corresponding bases for each location in the sample sequence. Proceeding in a columnar manner, corresponding basecalls for a plurality of sequence fragments 550 may be associated and the information assessed to generate a consensus basecall. The consensus basecall is representative of the combined information which may be used to improve the accuracy and degree of confidence for identification of the composition of the final sample sequence. In various embodiments the consensus-calling method 800 desirably incorporates a rule-based approach that may be readily modified to allow further development and selective tuning thereby improving the flexibility and potential accuracy with which basecalls may be made.

Commencing in state 805, sample input is collected which may include the aforementioned sample assembly input 405, as well as any data and information generated during the preprocessing operations 505. The sequence information is thereafter aligned so as to permit columnar analysis for each basecall position in the sample sequence. In state 807, the basecall information contained in an identified column of sequence information is evaluated for gaps. Sequence gaps occur where a particular base (or mixed-base) cannot be identified with a desired or selected degree of confidence or certainty. Gaps may arise from various sources of sequencing error including mobility shifts and basecalling in areas with poorly resolved peaks. In one aspect, a gap may be representative of a position within a particular sequence fragment 305 where the base for a particular position is not readily identifiable.

In one aspect, the consensus-calling method 800 processes gaps by evaluating the basecall information for other sequence fragments 305 within the identified column. For each gap, a quality value may be assigned to the gap region in state 812. In one aspect, assigning quality values to identified gaps aids in evaluating the gap call confidence using other sequence fragments in consensus comparison of the columnar information. The quality value for the gap may further be assigned by determining the average of adjacent bases that may substantially flank the gap; to thereby yield a value representative numeric of the confidence level for the gap.

Evaluating the identified basecalls in the corresponding consensus column, the number of gaps in the column is then identified in state 809. If the gap number exceeds a preselected gap threshold (determined in state 810) then a gap may be called in state 815. The gap threshold may be defined as the ratio of gaps to non-gap (identifiable) bases within the column and may be represented by a numeric, fractional, or percentile value. In one aspect, the gap threshold may be selected to be between approximately 50%-75% wherein if the number of gaps to non-gap calls in the column exceeds the selected gap threshold, a gap is called in the assembled sample sequence.

If the gap threshold is not exceeded in state 810 the method 800 proceeds to state 820 where a base agreement determination is made. In one aspect, the base agreement determination comprises evaluating each of the basecalls for a selected column. In one aspect, if all of the basecalls in the column agree with one another then the basecall may be identified as the consensus call for the column in state 825. For example, if each of the basecalls for the column corresponds to the base 'G' then the consensus call for the sample sequence will be assigned as the base 'G'.

As previously described, a quality value may desirably be associated with each basecall. The quality value may further reflect a calculated degree of confidence with which the basecall is made and, therefore, may serve as an indicator of sample sequence accuracy.

In various embodiments, the quality value for a consensus call wherein all of the bases are in agreement as described above may further be identified by the following equations:

$$\text{Equation 2: } Q_{cons} = \sum_i \left(\frac{1}{N-1}\right) \sum_{j \neq i} \varepsilon_{ij} Q_j$$

$$\text{Equation 3: } \varepsilon_{ij} = \frac{N-1}{N} \gamma_{ij} + \frac{1}{N}$$

In these equations N represents the number of overlapping sequence fragments for a particular column in the consensus, where both sums are calculated over the sample number. $Q_{cons}$ further represents the quality value assigned to the consensus call and Q represents the quality value for sample. In these equations, $\varepsilon_{ij}$ represents a weight derived from the degree of independence for each of the quality-value estimates. In one aspect, the value $\varepsilon_{ij}$ may be used to avoid over weighting of redundant calls. Redundant calls may arise; for example, in instances where a plurality of sequencing traces undergoing analysis contain regions of substantially elevated degrees of similarity.

Furthermore, $\gamma_{ij}$ is a derived parameter defined according to Equation 4 below which generally ranges from approximately 0 to 1. This value may further be used to express the degree to which information from samples i and j are independent. In one aspect, for two sequence fragments aligned in opposite orientations (e.g. 5'-3': 3'-5'), this parameter may be set to a value of '1' whereas for sequence fragments oriented in substantially the same direction, this parameter may be set to a value of '0'. In one aspect, use of this parameter aids in representing the notion that the quality of calls obtained from samples sequenced in the forward and reverse orientations may be uncorrelated.

For two overlapping samples sequenced in the same orientation the following relationship may further be identified:

Equation 4: $\gamma_{ij} = \dfrac{\Delta_{ij}}{\Delta_{max}}$

Here, $\Delta_{ij}$ represents the absolute difference in basecalls between the position of the basecall in sample i and the position of the basecall in sample j. Additionally, $\Delta_{max}$ is a parameter that may be used to select how far apart the position in two samples should be before the quality of the two calls may be considered to be statistically independent. In one aspect, the value for $\Delta_{max}$ may range from approximately 50 bp.-200 bp. The parameter $\gamma_i$ may further be set with a value of '1' if $\Delta_{ij} > \Delta_{max}$.

It is observed that quality value assignment according to the relationships described by Equations 2 and 3 provides several desirable properties. In one aspect, when the quality values for each basecall within a particular column are substantially independent, it may be determined that $\gamma_{ij}=1$ and as a result, $$Q_{cons} = \sum_i Q_i.$$

In this instance, the following relationship may be used to represent the consensus quality value:

Equation 5: $Q_{cons} = -10 \log p_{cons}$

In this equation $p_{cons}$ reflects the probability that the consensus call is an error and using this information, the consensus quality value may be determined from the logarithmic relationship. In one aspect, the equation has been found to apply when the sequence fragment quality values are statistically uncorrelated and, therefore, may be useful to determine when calculating the consensus quality value.

While this equation may be used in certain circumstances, a potential difficulty may be encountered when applying this relationship to evaluate quality values for redundant sequence information present in a selected column of consensus information. In such an instance, the quality of the consensus call for redundant sequence information may be overestimated without further analysis. For example, when substantially similar electropherogram information corresponding to redundant sequence fragments generated by similar PCR and sequencing primers are included in the same column assembly, there may be a tendency to overestimate the quality value when calculating it according to the aforementioned relationships. Typically, basecalls arising from redundant sequence fragments are highly correlated where a mistake or inaccuracy that has been made in the basecalls for one sample may also be made in the basecalls for a second sample. Therefore, the resultant quality values, if summed, may result in an overestimation of the true quality of the call. The present teachings overcome this tendency towards overestimation by applying an alternative relationship when dealing with highly correlated (e.g., redundant) basecalls.

In one aspect, using the relationship described in Equation 3, substitution of $\gamma_{ij}=0$ into this equation generates a reduced expression $$\varepsilon_{ij} = \dfrac{1}{N}.$$

Substitution of this expression into Equation 2 therefore reflects an average of the quality for the sequence fragments without undesirable overestimation. Therefore, use of the independence parameter, $\gamma_{ij}$ provides a means to generate a superior estimate for redundant samples using the relationships shown in Equations 2 and 3 as compared to that provided by Equation 4.

In another aspect, the consensus sequence method avoids false negative basecalling in state 825 by screening for the presence of potential mixed-bases that may not have been previously detected or identified in the sample sequence input. False negatives correspond to true mixed-basecalls that may have been identified as pure-bases. False negatives may further generate undesirably high quality values if directly calculated using the relationships shown in Equation 2 and 3. The screening process therefore desirably helps to avoid quality value assignment that may inaccurately reflect the basecall confidence. When possible mixed-bases are found by the screening process, the same pure-basecall may still be called, however, the quality value associated with the call is adjusted accordingly in state 875 to reflect a lower quality or confidence level. In one aspect, adjustment of the quality value for a possible mixed-base depends on the result of the relationship shown in Equation 5 which will be described in greater detail hereinbelow.

For basecalls that are determined not to be in agreement in state 820, the method 800 proceeds to state 830 where a more rigorous evaluation of mixed-bases is performed. In one aspect, it is desirable to perform a rigorous evaluation of mixed-bases in this state 810 in order reduce the number of false positives that might otherwise be called at the single strand level and which might persist during consensus calling. In one aspect, an increased number of false positives persisting in the assembly are undesirable as they may be carried over to the consensus sequence. Therefore, rigorous evaluation of mixed-bases in state 830 is desirable to overcome some of the conventional difficulties encountered when assigning mixed-basecalls.

In many conventional approaches, mixed-basecalls may be resolved by estimating the quality of the mixed-basecall versus a pure-basecall at the same location or column and thereafter selecting the higher quality call. While this approach may produce the correct basecall at the single-strand level (e.g. for single sequence fragments), there is a likelihood of missing difficult or elusive mixed-bases using this approach. In one aspect, conventional analysis methods may improperly call mixed-bases when a single pure-base component predominates over other bases in the electropherogram. In various embodiments, the present teachings overcome this difficulty due, in part, to the availability of the plurality of basecalls for each column. Using the multiplicity of basecalling information, the rigorous evaluation used to identify mixed-bases may produce superior results as compared to conventional methods.

According to state 830, a threshold parameter may be designated between approximately 5-30%. In one aspect, this parameter is selected to aid in the identification of smaller mixed-base peaks while potentially avoiding larger peaks that may be associated with false positive calls. Previously identified mixed-bases may then be recalled and evaluated using the more rigorous approach. In various embodiments, the approach may comprise evaluating the recalled mixed-bases to determine a modified quality value according to the following relationship:

Equation 5: $\delta + \lambda \dfrac{\beta_0 - \beta}{1 - \beta}$

This equation comprises a scaling factor for which previously identified quality values may be multiplied by to generate the modified quality value. In various embodiments, this relationship helps to avoid undesirably high quality value assignment for missed mixed-bases (e.g. false negatives). In one aspect, application of the scaling factor desirably reduces the quality values for pure-bases in the column when a mixed-base has been called.

In this equation, $\delta$ and $\lambda$ represent empirically determined parameters, $\beta_0$ represents the threshold that the mixed-base was identified at, and $\beta$ reflects a selected minimum threshold for identifying mixed-bases according to the method 800. Exemplary ranges for each of these parameters correspond approximately to $\delta=0.1\text{-}0.5$, $\lambda=0.2\text{-}0.9$, and $\beta=0.01\text{-}0.30$. In one aspect, the threshold may be expressed as a percentage of a primary peak height found in the electropherogram. In another aspect, scaling by the factor obtained from Equation 5 desirably reduces the quality value of recalled mixed-bases with smaller secondary peaks, while allowing a relatively high quality value for recalled mixed-bases with higher secondary peaks.

After the mixed-bases are recalled using the more rigorous approach, the basecalls are checked for agreement in state 835. If the basecalls are determined to agree then the consensus basecall may be assigned as the agreeing basecall in state 840 and the quality value may be determined according to Equations 2 and 3 described above.

In those instances where the basecalls compared in state 835 are determined not to agree, the method proceeds through a series of additional operations shown in FIG. 8B. In one aspect, consensus base assignment is made for non-agreeing basecalls using a voting approach that may be used to resolve the conflicting basecalls. According to state 850, a basecall vote is generated which may be used to ascertain the predicted correct call. In various embodiments, the basecall vote may comprise evaluating the conflicting call $\alpha_i$ using the summation illustrated below:

Equation 6: $s_{\alpha_i} = \sum_i c_j$

In this equation, the summation of basecalls is taken over an identified sample set comprising one or more basecalls to generate a value associated with the conflicting call $\alpha_i$. Additionally, the individual sample vote $c_j$ may be defined according to the following relationships depending upon the nature of the basecall. For example, when the basecall is associated with a pure-base, the individual sample vote may be determined according to the following equation:

Equation 7: $c_j = \epsilon QV$

In this equation, $\epsilon$ is a scaling parameter that may be used to increase the vote weight for pure-bases. In one aspect, the value of $\epsilon$ may be between approximately 1.50-2.00. In one aspect, this equation may be applied to offset the statistical limitation that a quality value assigned by conventional basecalling applications may be excessively high for mixed-basecalls compared to similar quality values for pure-basecalls. Additionally, application of this equation may desirably aid to reduce the false-positive rate of the consensus-calling methodology thereby allowing a lower mixed-base threshold to be used for the single-strand basecalling. Application of this relationship may further be used to moderate the number of false negatives by adjusting the quality values for each basecall to better balance mixed-basecall and pure-basecall quality values.

In another aspect, the individual sample vote $c_j$ may be defined according to another relationship when the basecall comprises a mixed-base.

Equation 8: $c_j = \kappa QV$

In this equation, $\kappa$ is a scaling factor which may be used to decrease the vote weight for mixed-basecalls. In one aspect, this equation may be additionally used to reduce the mixed-base vote in the presence of local mixed-base noise (previously defined above). For example, by defining x as the local mixed-base noise at the basecall position of interest, then $\kappa=(1-\eta)[(1-\eta)(1-x^{3/2})+\eta-\eta x]+\eta$ where $\eta$ is a parameter which approximates how much the vote may be lowered for mixed-basecalls made in the presence of local mixed-base noise. In various embodiments, the value of $\eta$ may be selected from between approximately 0.1-0.5.

In one aspect, the false positive rate may further be reduced by assigning a weight of $(1-\kappa)QV$ to the primary peak associated with the mixed-basecall. Furthermore, if the mixed-basecall was identified in state 830 then a weight of approximately $0.5\epsilon QV$ may additionally be added to the primary peak basecall. This approach may be used to desirably reduce the false positive rate for the rigorous bases calls made in this manner.

The aforementioned summation indicated by Equation 8 may additionally be weighted for the presence of basecalls made in the same orientation. In one aspect, two or more samples in the same orientation may provide redundant estimates of the appropriate basecall. To offset this effect, a differential weighting of the redundant basecalls may be made. For example, the highest quality call in each orientation may be assigned with a weight of approximately '1' and other identical calls in the same orientation may be assigned with a weight of approximately '0.5'.

Upon completion of the aforementioned analytical steps, the basecall with the greater or substantially maximal vote may be selected by the consensus-calling routine in state 855. Subsequently in state 860, the consensus calling routine proceeds to perform a basecall validation check. The basecall validation check is used to verify that the consensus basecall is substantially supported by each of the samples in the assembly. In one aspect, if the call is a mixed-basecall this check may involve verifying that each of the samples has at least some degree of signal present at this position in the electropherogram. If it is determined that there is support of the mixed-basecall in each of the samples then the basecall is finalized and a quality value generated in state 865. In one aspect quality value determination for the basecall assignment may proceed according to Equation 9 described in greater detail hereinbelow. In various embodiments the mixed-base validation operation performed in state 860 desirably aids in the determination of whether there is support for the mixed-base consensus call. This operation may additionally serve as a screen to reduce the occurrence of false positives.

In one aspect, mixed-based validation may comprise verifying that each of the sample fragments contributing to the basecall has a signal present at or above a pre-selected level, $\phi$. Furthermore, $\phi$ may be selected to be between approximately 1%-10% of the primary electropherogram peak amplitude. As previously described, should the consensus call pass the validation check, a quality value may then be assigned to the consensus call in state 865 according to the following relationship:

$$\text{Equation 9:} \quad Q_{cons} = \zeta s_{\alpha_{cons}} - \sum_{\alpha_i \neq \alpha_{cons}} s_{\alpha_i}$$

In this equation, $\zeta$ is a preselected weighting factor that may be used to express the degree of confidence in the selected vote with the summation taken over all of the votes not in favor of the consensus basecall. In one aspect, this relationship may produce a negative value which may further result in the consensus quality value being assigned to a selected minimum default value. In various embodiments, the weighting factor may be determined to represent a value between approximately 1.0-1.5.

If the mixed-base validation of state 860 fails then the method 800 proceeds to state 870 where a basecall intersection is determined. The mixed-basecall intersection may comprise evaluating each of the sample fragment basecalls that contribute to the consensus basecall. In one aspect, the intersection may be defined in a straightforward manner where the intersection between one or more pure-basecalls and one or more mixed-basecalls is determined. For example, in one exemplary comparison an intersection between an 'A' basecall (a pure-base) and an 'M' basecall (a mixed-base) results in an intersection base of 'A'. Likewise, the intersection between an 'S' basecall (a G/C mixed-base) and a 'W' basecall (an A/T mixed-base) produces the empty set. In one aspect, if the intersection is the empty set then the original consensus basecall may be assigned but with a quality value given by Equation 9 with all of the votes reduced by a predefined factor such as 0.5. If the intersection reflects a non-empty value (e.g. a basecall such as A, G, T, or C) then the quality value assigned to this new consensus basecall may be given by Equation 9 without the aforementioned reduction in quality.

Figure 9:
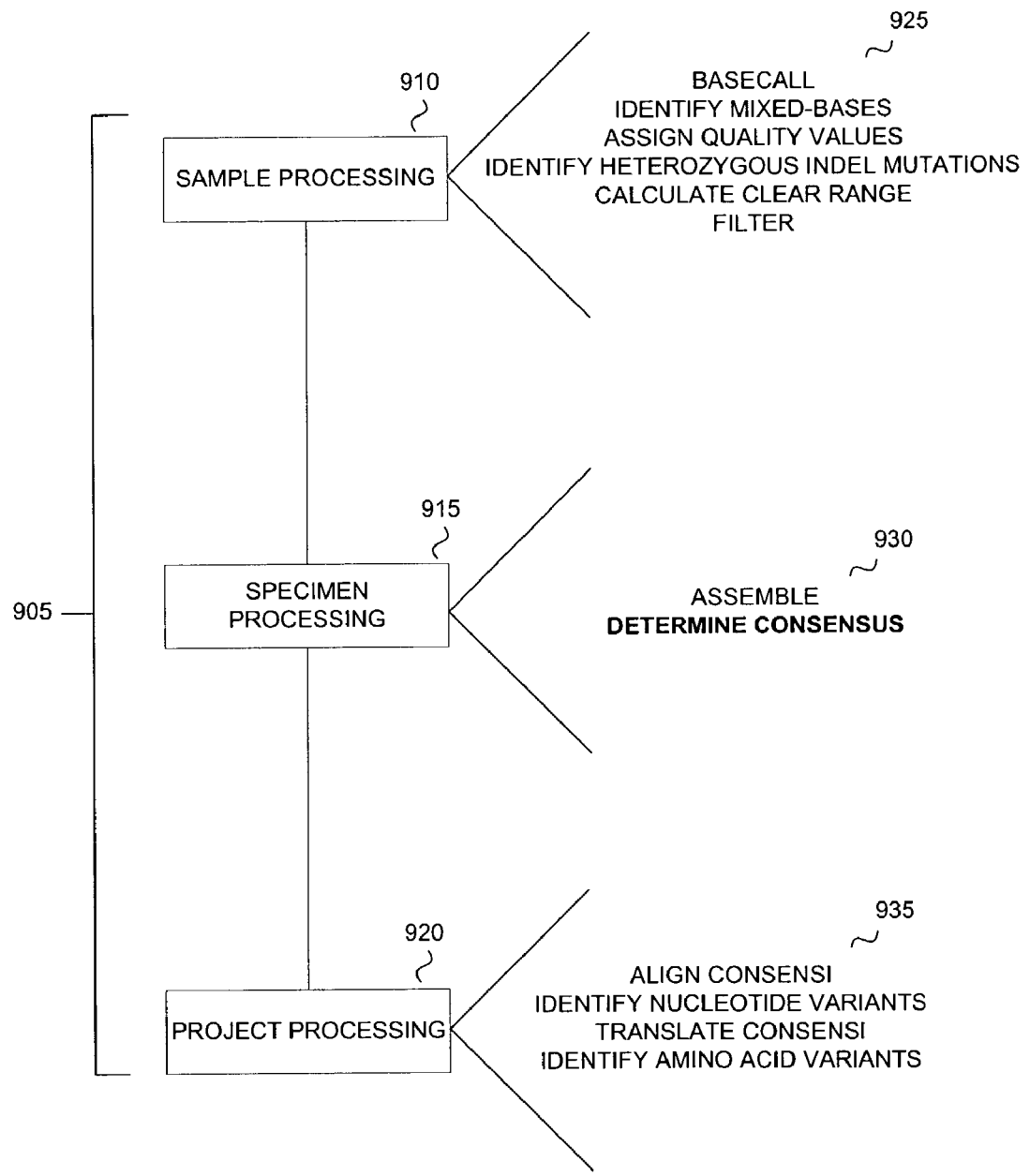
FIG. 9 is block diagram illustrating exemplary modules for a sequence analysis software application.

FIG. 9 illustrates an exemplary integration of the present teachings into a software application 900 directed towards sequence analysis (e.g. SeqScape and other sequencing and re-sequencing applications). In various embodiments, the software application 900 comprises one or more modules 905 which process input sequence data and/or trace information to identify/output one or more associated sequences. The modules 905 may further comprise a sample processing module 910, a specimen processing module 915, and a project processing module 920.

In one aspect, the sample processing module 910 may comprise functionality for receiving the input sequence data and/or trace information and thereafter performing operations 925 which may include: Basecalling, Identification of mixed-bases, Quality value assignment, Identification of heterozygous frameshift mutations, Clear range calculation, and Data filtering/Smoothing operations. Similarly, the specimen processing module 915 may comprise functionality for performing operations 930 associated with sequence assembly to thereafter be used in determination of one or more consensus sequences according to the methods described by the present teachings. The project processing module 920 may then provide functionality for performing post-consensus determination operations 935 including, for example: Aligning the one or more identified consensus sequences, Identifying nucleotide variants, Translating the one or more consensus sequences into amino acid or protein sequences, and Identifying amino acid or protein sequence variants.

Further details of these operations may be found in previous sections of the present teachings and the following commonly assigned U.S. patent applications which are hereby incorporated by reference in their entirety: application Ser. No. 09/658,161 filed Sep. 8, 2000 and entitled: A system and method for improving the accuracy of DNA sequencing and error probability estimation through application of a mathematical model to the analysis of electropherograms; Provisional Application Ser. No. 60/371,641 filed Apr. 10, 2002 and entitled: Method to Detect and Identify Heterozygous Frameshift Mutations Using Direct Sequencing along with its corresponding non-provisional application (Serial Number to be assigned).

It will be appreciated by one of skill in the art that the aforementioned modular arrangement may be executed in numerous different manners such as using more or less modules, performing additional operations, performing some, but not all, of the aforementioned operations, and other variations to be used in sequence analysis applications. As such, these variations are considered but other embodiments of the present teachings.

The above-described teachings present novel methods by which sequence analysis basecalling may be performed. In various embodiments, use of these methods may improve the accuracy of automated systems that are designed for high-throughput sequence analysis. It is conceived that these methods may be adapted for use with numerous sequencing applications including, but not limited to, heterozygote detection, single nucleotide polymorphism analysis, and general sequence assembly tasks. Additionally, these methods may be readily integrated into new and existing sequence processing applications, software, and instrumentation.

In various embodiments, sequence analysis software applications that integrate the methodology described herein yield highly accurate basecalls with a low observed error rate. For example, these methods have been integrated into the SeqScape™ software application for variant identification and resequencing (Applied Biosystems, CA) and found to perform with an error rate at or below 1% even with diverse data sets which may include conventionally problematic data such as experimental or systematic noise, dye blobs, and mobility shifts.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A software-implemented method for consensus basecall analysis used for sequence identification and quality assessment, the method comprising:

receiving input sequence data as nucleotide base assembly information for at least one sequence fragment wherein the assembly information comprises a plurality of putative basecalls spanning at least a portion of the sample sequence, wherein each putative basecall comprises a pure-basecall indicative of a single nucleotide base, a mixed-basecall indicative of two or more nucleotide bases, or a gap indicative of a region lacking an identified nucleotide base, the assembly information further comprising a plurality of per-base quality values associated with the plurality of putative basecalls;

performing a recalling operation on selected mixed-basecalls determined on the basis of quality values associated with the selected mixed-basecalls;

performing a consensus calling operation wherein the putative basecalls are aligned to generate the consensus sequence representative of a predicted base sequence for the sample sequence;

performing a consensus quality value determination wherein for each base of the consensus sequence a consensus quality value is calculated using the per-base quality values associated with that base, the consensus quality value reflective of the confidence in the consensus basecall for that base; and outputting the consensus quality values for the input sequence data wherein the consensus quality values reflect the confidence in sequence identification of the consensus basecall analysis.

2. The method of claim 1, wherein each per-base quality value represents a calculated degree of confidence in the putative basecall being correct and the recalling operation performed for selected mixed-basecalls improves confidence in mixed-basecall accuracy.

3. The method of claim 2, wherein putative basecalls that are mixed-basecalls are further evaluated by:

evaluating peak characteristics associated with each mixed-basecall to identify mixed-basecalls whose peak characteristics exceed a selected threshold; and recalling each mixed-basecall whose peak characteristics exceed the selected threshold using a rigorous basecalling operation to generate a modified quality value for that mixed-basecall.

4. The method of claim 3 wherein the rigorous basecalling operation further comprises applying a scaling factor to each mixed-basecall according to the relationship:

$$\delta + \lambda \frac{\beta_0 - \beta}{1 - \beta}$$

wherein $\delta$ and $\lambda$ represent empirically determined parameters, $\beta_0$ represents a threshold associated with the mixed-basecall based on its peak characteristics, and $\beta$ reflects the selected threshold.

5. The method of claim 1, wherein the recalling operation identifies potentially erroneous basecalls, including false positive and false negative mixed-basecalls, that are screened prior to generating the consensus basecall.

6. The method of claim 1, wherein quality values for putative basecalls that undergo the re-calling operation are adjusted by applying a scaling factor which reduces the quality value, the scaling factor selected on the basis of the basecall composition.

7. The method of claim 6, wherein the re-calling operation for mixed-basecalls further comprises checking for basecall agreement, and thereafter assigning an agreeing basecall as the putative basecall.

8. The method of claim 7, wherein a quality value is determined for the agreeing mixed-basecall.

9. The method of claim 7, wherein basecalls that are not in agreement are identified and resolved using a basecall voting approach.

10. The method of claim 9, wherein the basecall voting approach comprises evaluating the quality values of the aligned basecalls, applying a differential weight to each of the basecalls, determining the higher quality basecall, and thereafter assigning the consensus basecall as the higher quality basecall.

11. The method of claim 10, wherein the differential weight applied to each of the basecalls is based, in part, upon whether the basecall is a pure-basecall or a mixed-basecall.

12. The method of claim 10, wherein the differential weight applied to each of the basecalls is based, in part, upon a relative constituent composition for each base which makes up the mixed-basecall.

13. The method of claim 10, wherein the differential weight applied to each of the basecalls is based, in part, upon the presence of redundant basecalls in the aligned putative basecalls.

14. The method of claim 7, further comprising validating the mixed-basecall to determine if the mixed-basecall is supported by each of the aligned putative basecalls.

15. The method of claim 14, wherein a mixed-basecall supported by the aligned putative basecalls is assigned as the consensus basecall.

16. The method of claim 14, wherein an intersection is determined for mixed-basecalls not supported by the aligned putative basecalls.

17. The method of claim 16, wherein the intersection for the mixed-basecalls is assigned as the consensus basecall.

18. The method of claim 16, wherein for mixed-basecalls which lack an intersection, one of the mixed-bases is selected as the consensus basecall.

* * * * *